US006287570B1

(12) United States Patent
Foley

(10) Patent No.: US 6,287,570 B1
(45) Date of Patent: Sep. 11, 2001

(54) VACCINE AGAINST SWINE INFLUENZA VIRUS

(76) Inventor: Patricia L. Foley, 55789 Oak Blvd., Huxley, IA (US) 50124

(*) Notice: Subject to any disclaimer, the term of this patent is extended or adjusted under 35 U.S.C. 154(b) by 0 days.

(21) Appl. No.: 09/197,679

(22) Filed: Nov. 23, 1998

(51) Int. Cl.[7] ........................ A61K 39/12; A61K 39/285; C12N 7/01

(52) U.S. Cl. .................... 424/199.1; 424/93.1; 424/93.2; 424/232.1; 435/235.1

(58) Field of Search ........................ 435/235.1; 424/93.1, 424/93.2, 199.1, 232.1; 536/23.1, 23.72

(56) References Cited

U.S. PATENT DOCUMENTS 5,676,950 * 10/1997 Small, Jr. et al. ................ 424/199.1

OTHER PUBLICATIONS

Sutter et al. A Recombinant Vector Derived from the Host Range–Restricted and Highly Attenuated MVA Strain of Vaccinia Virus Stimulates Protective Immunity in Mice to Influenza Virus. Vaccine, vol. 12, pp. 1032–1040, 1994.*

* cited by examiner

*Primary Examiner*—Deborah J. R. Clark
*Assistant Examiner*—Janet M. Kerr
(74) *Attorney, Agent, or Firm*—Glenna Hendricks; M. Howard Silverstein

(57) ABSTRACT

This invention provides a vaccine for protecting swine against influenza virus by administration of an attenuated recombinant vaccinia virus containing inserts of the hemagglutinin (HA) and nucleoprotein (NP) genes of influenza virus, which express the hemagglutinin and nucleoprotein proteins.

4 Claims, No Drawings

VACCINE AGAINST SWINE INFLUENZA VIRUS

FIELD OF THE INVENTION

This invention provides an attenuated recombinant vaccinia virus containing inserts of hemagglutinin (HA) and nucleoprotein (NP) genes from swine influenza virus.

BACKGROUND OF THE INVENTION

Many pathogenic viruses, against which vaccines would be desirable, are simply too proficient at producing disease to be administered in a live product from the naturally-occurring organism. Furthermore, even when a virus strain does not itself produce disease, it may have characteristics that, when recombined with those of another strain encountered in the field, result in a far worse disease outbreak. Such is the case with influenza viruses, which have a segmented genome capable of reassortment. If an attenuated vaccine strain with certain gene segments that give it the ability to replicate well in a given host species should exchange segments with another virulent strain that does not replicate well in that species, the outcome may be a new strain that is both virulent and well-adapted to the new host. That was the fear that existed at the time of the 1997 Hong Kong outbreak in humans of an avian strain of influenza. Fortunately, although the avian strain was able to colonize certain humans, it did not replicate well enough in that host to cause an epidemic in what would have been a completely susceptible, immunologically naive population.

Among the veterinary influenza products, there are eight avian vaccines manufactured by one company. One swine vaccine and five equine vaccines produced by six different companies. They are all killed virus products, as are the human influenza vaccines used in annual vaccination programs. Human vaccines are changed annually to reflect the newly emerging strains and frequently contain 3 distinct hemagglutinin antigens from diverse strains to maximize protection against disease.

One problem with inactivated influenza virus vaccines is that the immunity generated is only partial. In the presence of a strong adjuvant, antigens can stimulate B-cells and induce a good humoral response. However, there is little cell-mediated immunity generated by a killed product. This can mean the difference between disease and full or partial protection. Furthermore, the immunity provided by a killed product can be relatively short-lived. The potential advantages of a recombinant vaccine, when administered in a safe vector, are that it may express protective immunogens against even the most dangerous of viruses, provide both humoral and cell-mediated immunity, and extend the duration of that protection beyond the time provided by a killed product.

The pathology induced by SIV occurs throughout the respiratory tract and consists of acute inflammation, edema, and necrosis. More severe complications, in the form of interstitial pneumonia, thickening of alveolar walls, hyperemia, thrombosis, hemorrhage, and necrosis, can occur. Lung lesions tend to be bilaterally distributed, predominantly in the cranial and middle lobes. Generally, most pigs recover but resolution of lesions may take up to a month.

In recent years there have been periodic occurrences of 'atypical' SIV outbreaks, leading to speculation that the relatively stable antigenic profile of SIV may be changing. Reports have appeared in the literature since 1992 which indicate regarding the occurrence of SIV either associated with unusual signs or exhibiting more virulence than expected. First, there was a report from Quebec regarding an H1N1 variant producing proliferative and necrotizing pneumonia in pigs. Some symptoms were very similar to those seen arising from infection with the PRRS virus. More point mutations and diversity were observed than are usually seen in North American SIV isolates. Another novel isolate from a severely affected herd was designated A/Sw/Nebraska/1/92. That strain induced persistent, high fevers (up to 42° C.) but not much respiratory disease. Given the high degree of conserved sequences in typical SIV strains isolated in the U.S., it was surprising that the most closely related reference H1N1 strain had only 94% identity at the nucleotide level and 96% identity at the amino acid level to this SIV isolate. Nonetheless, it was closer genetically to 'classical' H1N1 SIV than to avian or human H1N1 viruses. In England, an H1N1 strain antigenically distinguishable from classic SIV and European avian-like H1N1 viruses caused a sudden increase in SIV cases, but still resulted in the usual clinical signs of coughing, sneezing, and anorexia. However, upon experimental infection, this strain produced a more severe interstitial pneumonia and hemorrhagic lymph nodes.

The significance of the genetic diversity represented by these strains is as yet undetermined. It may be that there are no 'atypical' SIV strains, merely a greater degree of potential antigenic diversity among field strains than previously detected. It is known, however, that subtype H1N1 influenza viruses have been circulating continuously in U.S. pigs for over 60 years. It is believed that the great pandemic of "Spanish flu" in 1918/19, the worst in history, killing at least 20 million people worldwide, was either caused by a swine virus or by a human strain that entered the pig population at that time. In 1997, RNA from a casualty was extracted from formalin-fixed, paraffin-embedded tissue and sequenced. All sequences determined were very similar to those of classic H1N1 SIV, suggesting that human and swine strains share a common avian ancestor, existing some time before 1918.

Northern Europe saw its first isolate of SIV in 1978/79, and although in H1N1 virus the H1 was similar to the avian H1, it is but distinct from both human and swine H1. Since then, there have been instances where an avian virus has been able to cross species and infect the pig population, as with SwGer/81. There are also and cases where reassortment between avian and classical SIV has occurred, such as is seen with SwHK/82. In addition, there is a human virus-like H3N2 subtype that has been isolated on occasion in European pigs since 1980. this may result from the 1968 antigenic shift and an ability of the H3N2 to persist in pigs even when not circulating in the human population. It is interesting that a serological survey conducted in 1988–1989 in U.S. pigs found evidence of H3 viruses antigenically similar to the human H3 strains, which was current at that time, at about 1.1% average prevalence. In addition, a serological survey during 1976–1977 detected an incidence of 1.4% for H3N2 infections. Moreover isolation from one herd of a virus antigenically similar to a human H3N2 strain was reported in that study. However, complete sequencing to determine whether the isolate was of human origin was not performed. However, no H3 human strain has been confirmed as present in U.S. pigs. Very recently, the National Veterinary Services Laboratories identified an influenza virus subtype H3N2 isolate from a swine breeding herd in North Carolina (personal communication). Studies are currently underway to determine species of origin and other characteristics of the virus.

In summary, it is recognized that there are at least three HA subtypes circulating in pigs at present, classic SIV H1, avian virus-like H1, and human virus-like H3. These have been found in various permutations of SIV gene segments. One, an H3N1 strain, appeared to be a combination of the classic SIV and the human virus-like H3N2 found in swine. Another, an H1N2 isolate believed to be from a human H1N1 and the swine-adapted H3N2, caused clinical disease in pigs. Still another represented a reassortment between human and avian strains in symptomatic Italian pigs, providing the first proof that pigs can act as 'mixing vessels' for human and avian viruses.

The critical role that pigs can play in pandemics was underscored by the discovery that children in the Netherlands were sick from avian-human influenza virus generated in pigs, transmitted pig-to-person, and person-to-person. Normally, avian strains do not replicate in humans, and human strains do not replicate in birds. This is a function of their specific sialyloligosaccharide receptors on the surface of epithelial cells of the upper respiratory tract. In a previous study, it was determined that, of 38 avian influenza strains, fully 31 were successfully transmitted to swine. Every HA subtype (of 14 tested) had at least one strain that grew as well as a swine or human virus. Since then, it has been determined that pigs, in fact, have both avian- and human-specific viral receptors present in their upper respiratory tract and that some avian strains, with continued replication, acquire the ability to recognize human receptors as they become swine-adapted. Taken together, these data delineate the danger to humans of a pig population unprotected against influenza. If an avian virus with a non-human-type HA is introduced into pigs, then reasserts with a human strain, a pandemic among complete susceptibles would occur. Although direct interspecies spread from bird to human can happen, as was seen with the 1997 Hong Kong H5N1 cases, the virus under those circumstances may not readily adapt to its new host and relatively few may be affected. The dangers may be greater when interspecies transmission occurs with the pig, able to be infected by either avian or human strains serving as a 'mixing vessel', wherein gene segments from different strains reassort to produce new viruses. Clearly, a safe, live vaccine vector able to express multiple genes that could be given frequently to boost or provide new immunity,.would be helpful.

Vaccinia virus, a member of the Orthopoxviruses, is known to be a strong inducer of humoral and cell-mediated immunity. Vaccinia virus has been used as an experimental vector in several species and in accidental human exposure, with considerable documentation of its ability to induce immunity to several diseases. The first reports of its use as a vector for the delivery of immunogens surfaced in the early 1980's. By 1990, there were numerous reports in the literature regarding its successful expression of the hepatitis B virus surface antigen, the thymidine kinase and glycoprotein D from herpes simplex virus, the influenza hemagglutinin, human respiratory syncytial virus glycoprotein G, and the rabies virus glycoprotein. Several studies demonstrated its immunogenicity in humans. Insertion of more than one gene was also accomplished. For example, one recombinant expressing both the hepatitis B virus surface antigen and the herpes simplex virus glycoprotein D was produced, thus raising the possibility of using a single vector expressing immunogens from multiple pathogens, thereby providing protection against all of them with a single vaccine.

As promising as vaccinia virus seemed to be for certain applications, it had several drawbacks which limited its potential for general use. During the smallpox eradication effort, vaccinia caused unwelcome side effects. Apart from the localized irritation induced by the inoculation, there were more severe complications among the immunocompromised. It was estimated that one in every million vaccinations resulted in death. For this reason, vaccinia virus was no longer used clinically in the U.S. or the rest of the world following the end of smallpox vaccination. Following decades of little to no use, the general population, at one time well exposed, has now become quite susceptible, as people less than roughly 30 years of age have no immunity. Unfortunately, this risk of human exposure greatly curtails the usefulness of the naturally occurring vaccinia as a vector. Even if a vaccine were designed for some one species in the veterinary market, because vaccinia has such a wide host range, there exists the potential for inadvertent inter-species spread.

To circumvent the problems associated with vaccinia virus, yet retain its advantages, researchers have investigated strains of vaccinia virus that are attenuated, either by nature or design. One such modified strain, Ankara (MVA), has been widely studied. The strain was originally developed from the vaccinia virus Ankara strain as a safe alternative for smallpox vaccination, and has been used without significant side-effects in over 120,000 people, including young children and the elderly, for immunization against smallpox. After approximately 570 passages in primary chick embryo fibroblasts (CEF), it has lost its ability to replicate or at least to replicate well in numerous mammalian cell lines. It contains six major deletions that prevent virus assembly in almost all mammalian cells tested. However, gene expression, both early and late, remains relatively unimpaired. The exact nature of this host restriction is not really understood. Thus far, four orthopox virus host range genes have been documented. These are designated CHOhr, C7L, K1L, and E3L genes. Of these, only the function of the E3L gene, which expresses an RNA binding protein, is known. Compared to its parental strain, MVA has deletions that consist of about 15% (30,000 base pairs) of its former genome, including deletion of most of the K1L gene. Interestingly, one study showed, replacement of the K1L gene in MVA removed only the host restriction in RK13 cells. This suggests that there are multiple, cumulative genetic defects in MVA replication. If so, as seems likely the probability of spontaneous reversion to a wild type host range is quite low. It can be assumed, therefore, that the deletions greatly increase the safety of MVA for use as a vaccine vector.

SUMMARY OF THE INVENTION

This invention provides means for protecting swine against influenza virus by administration of an attenuated recombinant vaccinia virus containing inserts of the hemagglutinin (HA) and nucleoprotein (NP) genes of influenza virus, which express the hemagglutinin and nucleoprotein proteins. In the instant case, the virus used was from a field isolate of swine influenza virus (SIV). The recombinant virus (MVA/SIV) vaccine induced both humoral and cell-mediated immune responses against SIV.

DETAILED DESCRIPTION OF THE INVENTION

The vaccine of the invention provides protection from influenza infection. The particular invention relates to administration of novel recombinant vaccinia to swine. Moreover, by protecting pigs from infection, the human population is protected from transfer of infection from swine to the human population. The vaccine of the invention was made by genetic engineering means. Generally, HA and NP genes of SIV were amplified by reverse transcription polymerase chain reaction (RT-PCR) and cloned. These genes were sequenced and subcloned into a transfection vector that facilitated insertion of the SIV sequences into the genome of the modified vaccinia virus Ankara (MVA) strain of vaccinia virus. Plaques were screened for HA and NP protein expression, purified, and expanded. Thirty pigs of mixed sex were placed into five groups of six pigs each. Two groups were vaccinated with the MVA/SIV recombinant, one intramuscularly (IM) and the other intranasally (IN), at 20–22 days of age. Another two groups were vaccinated with an MVA recombinant containing HA and NP genes from the human strain A/PR/8/34 (PR8), again one IM and the other IN, at the same dosage. Those four groups were reinoculated at 34–36 days of age. At 49–52 days of age, all 30 pigs, including the fifth group of 6 nonvaccinated controls, were oronasally challenged with the homologous SIV strain, using a nebulizer. The pigs were monitored and nasal swabs collected until day 5 postchallenge, at which time the pigs were euthanized and postmortem lesions examined grossly, histologically, and by immunohistochemistry for the presence of SIV.

Materials and Methods

Construction of the Recombinant

Genomic RNA from the ISU SIV isolate was purified from infected allantoic fluid using the PURESCRIPT™ RNA isolation kit (Gentra), in accord with the instruction provided therewith. HA- and NP-specific primers were used in a TITAN ONE-TUBE™ RT-PCR reaction (Boehringer Mannheim) to generate first strand cDNA, then amplified to double-stranded DNA. The RT-PCR products were cloned into the CLONEAMP™ pAMP1 System vector (GibcoBRL) for sequencing and subcloning into the JS5 plasmid vector. JS5 contains the same double promoters in opposite orientation for dual-gene cloning but not the flanking MVA sequences as found in plasmid vector G06 (both vectors courtesy of B. Moss, Laboratory of Viral Diseases, NIAID, NIH). It also has more convenient restriction sites for gene insertion. Following proper insertion of the two SIV genes, the cassette was removed from JS5 and inserted into G06. Following PCR screening of transformed colonies, using HA- and NP-specific primers, plasmid DNA was cut with various enzymes to determine correct orientation. DNA from 4 clones was used in the presence of LIPOFECTAMINE PLUS™ reagent (Gibco BRL) to transfect MVA-infected cells. Cells were passed and positive plaques purified as previously described (Sutter G, Wyatt L S, Foley P L, Bennink J R, Moss B. A recombinant vector derived from the host range-restricted and highly attenuated MVA strain of vaccinia virus stimulates protective immunity in mice to influenza virus. Vaccine 1994;12(11):1032–40).

Cells and Viruses

Vaccinia virus strains MVA and MVA/PR8 were generously provided by B. Moss, Laboratory for Viral Diseases (LVD), National Institute of Allergy and Infectious Diseases (NIAID), National Institutes of Health (NIH). MVA/ISU was recently constructed in our laboratory, as described above, from an Iowa field strain of SIV isolated by the Iowa State University Veterinary Diagnostic Laboratory (courtesy of B. Janke). MVA, MVA/PR8, and MVA/ISU were grown at 37° C. and 5% $CO_2$ in the second passage of chicken embryo fibroblast cells, using M199 medium with F-10 nutrient mixture (M199/F-10), supplemented with 0.15% bactotryptose phosphate broth, 0.09% Na bicarbonate, 1% 200 mM L-glutamine, 25 U/ml e5 penicillin G potassium, 75 U/ml streptomycin sulfate, 0.1% gentocin, and 5% FBS.

A 1960's SIV field isolate, provided by the Diagnostic Virology Laboratory (DVL), National Veterinary Services Laboratories (NVSL), and the ISU field isolate were propagated in the allantoic cavity of 10-day-old embryonated chicken eggs at 37° C. for 72 hours. The mean egg infectious dose ($EID_{50}$) and hemagglutination (HA) units of these SIV lots were determined. In addition, a 24-hr-old monolayer of swine testicular (ST) cells, seeded at 2×105 cells/ml, and grown at 37° C., in 5% $CO_2$, using Minimal Eagle's Medium (MEM) with Earle's salts (Gibco cat. no. 41500-018), supplemented with 0.22% Na bicarbonate, 0.5% edamine, 1% 200 mM L-glutamine, 25 U/ml penicillin G potassium, 75 U/ml streptomycin sulfate, 0.1% gentocin, 1% sodium pyruvate, and 5% FBS, was used for SIV replication. At 24 hours after seeding, medium was decanted and the ST monolayer inoculated with virus in sufficient medium to cover the monolayer. Following virus adsorption for one hour at 37° C., fresh medium was added and the cultures incubated at 37° C. in 5% $CO_2$.

Titration of Viruses

For MVA and MVA recombinant virus titrations, 24-hour old CEF cells, seeded at $8\times10^5$ cells/ml in 60 millimeter (mm) tissue culture plates under conditions cited above, were prepared. Dilutions of virus were made in M199-F10 media containing 2% FBS. Growth medium on the 60 mm plates was decanted and 0.2 ml per dilution added. Plates were held at 37° C., 5% $CO_2$, for one hour, with rocking every 15 mins. The inoculum was then aspirated and the plates refed with 4 mls of 2×MEM containing 10% FBS, 1% 200 mM L-glutamine, 25 U/ml penicillin G potassium, 75 U/ml streptomycin sulfate, and 0.1% gentocin mixed in equal parts with 1.1% melted agar. The mixture was allowed to solidify in the plates, which were then incubated at 37° C., 5% $CO_{21}$ for 2 to 3 days. The agar was removed by washing gently with 0.01 M PBS, pH 7.2, and the plates fixed. MVA recombinant-inoculated plates were fixed in 1:1 acetone:methanol, reacted with primary antibody, then anti-mouse or anti-swine peroxidase-labeled is conjugate. The substrate used for these assays was metal enhanced DAB (Pierce, Rockford, Ill.). Recombinant virus titers were determined using insert-reactive anti-H1N1 SIV polyclonal antisera and anti-PR8 HA and NP monoclonal antibodies (courtesy of J. Yewdell, NIAID, NIH) as primary antibody, and expressed as plaque-forming units (PFU). MVA titers were determined using either cytopathic effect (CPE) or immunofluorescent assay (IFA). For the latter procedure, plates were fixed in 80% acetone. The primary antibody was a rabbit-origin anti-vaccinia virus polyclonal antisera, reacted with an anti-rabbit FITC-conjugate. The titers were expressed as fluorescent focal units (FFU). This IFA procedure was also used on the MVA recombinant virus-infected cultures, subsequent to the DAB immunoplaque assay, to determine the titer of non-expressing plaques.

For SIV titration on the ST cell line, 96-well plates were inoculated with 50 ul virus dilution per well, centrifuged at room temperature for 2 hours at 400×g, incubated at 37° C. in 5% $CO_2$, then read by CPE or IFA, using anti-H1N1 SIV polyclonal antisera, 5–7 days postinoculation.

Nucleotide Sequence Analysis

The nucleotide sequence of ISU SIV HA and NP genes has not been previously reported. The cloned genes were subjected to primer walking along both strands of DNA, starting with the Universal (-21M13) and Reverse ('R-2', M13-USB) primers, using the ABI Prism Model 377 DNA Sequencer (Perkin Elmer). Sequences generated were aligned, edited, and assembled using AutoAssembler (Perkin Elmer). HA and NP sequences from PR8 and A/Sw/IN/1726/88 (IN88), a 'classical' Type A H1N1 SIV, were retrieved from the GenBank database using the respective accession numbers for PR8 HA (J02143) and NP (J02147), and IN88 HA (M81707) and NP (L46849). Sequences were compared using Omiga 1.1 software (Oxford Molecular Group). Slight alterations were made in the retrieved sequences only when warranted. In one case, addition of a single 'T' at IN88 HA base 1629, converted an otherwise meaningless amino acid code into one that closely followed the code for ISU HA for the remainder of the protein sequence. Likewise, an apparent missing base at nucleotide 1630 in PR8 HA rendered the bases thereafter totally heterologous. If a 'missing' G (found in ISU and IN88 HA) is added, the homology is 83.4% up to amino acid 556, when the code again becomes scrambled. If the first 1629 bases (or 543 amino acids) only are compared, that is, without adding the G, then the amino acid homology is 83.1%. It was felt that this was close enough to the first figure to call at 83% homology.

The sequences of the inserts are:

SIV-HA atgaaggcaatactattagtcttgc-
tatatacattcacagccgcaaatgcagacacatta tgtataggttatcatg-
caaataattcaactgacactgttgatacagtactagaaaagaat gtaacag-
taacacactctgttaaccttctagaagacagacataacggaaaactatgtaaa
ctaagggggggtagccccattg-
catttgggtaaatgtaacattgctggatggctcctggga aacccagaatgt-
gaattactattcacagcaagctcatggtcttacattgtggaaacatct
aactcagacaatgggacatgttacccaggagatttcatcaattatgaagag-
ctaa- gagag cagttgagctcagtgtcat-
catttgaaaggtttgagattttccccaaggcaagttcatgg cccaaccat-
gaaacgaacagaggtgtgacggcagcat-
gtccttatgctggagcaaacagc
ttctacagaaatttaatatggctgg-
taaaaaaaggaaattcatacccaaagctcagcaaa tcctatgttaa-
caataaggagaaggaagtcctcgtgctatggggcattcaccatccacct
accagtactgaccaacaaagtctctac-
cagaatgcagatgcctatgtttttgtggggtca tcaaagtacaacaagaaat-
tcaagccagaaatagcaacaagacccaaggtgagaggtcaa
gcagggagaatgaactattactggacactagttgagcctggagacacaat-
aacatt- cgaa gcaactggaaatctagtggtaccaa-
gatatgccttcgcaatgaaaagaggttctggatct ggtattatcatttca-
gatacaccagtccacgattgtaatacgacctgtcaaacacccaaa
ggtgctataaacaccagcctcccatttcagaatatacatccagtcacaatt-
ggagaa- tgt ccaaaatatgtcaaaagtacaaaat-
tgagaatggctacaggattaaggaatatcccgtct attcaatctaggggc-
ctgtttggagccattgctggctttattgaggggggggtggacagga
atgatagatggatggtacggttatcaccatcaaaatgagcagggatcagga-
tatgc- agcc gaccgaaagagcacacagaatgccat-
tgacgggatcactaacaaagtaaactctgttatt gaaaagataaacaca-
caattcacagcagtgggtaaagaattcaaccacctggaaaaaaga
atagagaatttaaataaaaaggttgatgatggttttctggatgtttggacttac-
aat- gcc gaattgttggttctattggaaaatgaaa-
gaactttggattaccatgactcaaatgtgaag aacctatatgagaaagtaa-
gaagccagctaaaaaacaatgccaaggaaattggaaatggc
tgctttgaattttaccacaaatgtgat-
gacaagtgcatggagagcgttaaaaatgggact tatgattac-
cccaaatactcagaagaatcaaaac-
taaacagagaggagatagatggagta
aagctggaatcaacaaggatttacca-
gattttggcgatatattcaactgtcgccagttca ttggtacttgttagtctc-
cctgggagcaatcagtttctggatgtgctccaatgggtcttt acagtgca-
gaatatgtatttaaaattaggatttcagagacatga (SEQ. ID No. 1).

SIV-NP atggcgtctcaaggcaccaaacgat-
catatgaacaaatggagactggtggggaacgccag gatgccacagaaat-
cagagcatctgtcggaagaatgattggtggaatcggaagattctac atc-
caaatgtgcactgaactcaaacttagtgattatgagggacgactaattc aa-
aatagc ataacaatagagagaatggtgctctct-
gcttttgatgagagaaggaataaatacctagaa gagcatcccagtgctgg-
gaaggatcctaagaaaactggaggacccatatatagaagagta gacg-
gaaagtggatgagagaactcatcctttatgacaaagaagaaataa ggaga-
gtttgg cgccaagcaaacaatggtgaagatgcaa-
cagccggtcttactcatatcatgatttggcac tccaatctgaacgatgccac-
ctatcagagaacaagagcgcttgttcgcactggaatggat cccagaatgt-
gctctctaatgcaaggttcaacacttcccagaaggtctggggccgcaggt
gctgcagtgaaaggagttggaacaatag-
caatggagttaatcagaatgatcaaacgtgga atcaatgaccgaaact-
tctggaggggtgaaaatgggcgaaggacaaggattgcatatgaa agaat-
gtgcaatattctcaaaggaaagtttcagacagctgcccagaggg
caatgat- ggat caagtaagagaaagtcggaacccag-
gaaatgctgaaattgaagatctcattttcctggca cggtcagcacttat-
tctaagggggtcagttgcacataagtcttgcctgcctgcttgtgtg
tatgggcttgcagtagcaagtgggcat-
gactttgaaagagaaggatattcactggtcggg atagaccccttcaaat-
tacttcaaaacagtcaagtgttcagcctgatcagaccaaatgaa
aacccagcccacaaaagtcaattggtgtggatggcatgccactctgctgc-
attt- gaggat ttaagagtatcaagcttcataagagg-
gaagaaagtggttccaagaggaaagctttccaca agaggggttcagat-
tgcttcaaatgagaatgttgaagctatggactctagtaccctagaa ctaa-
gaagcagatactgggccataaggaccagaagcggaggaaatacc aatc-
aacagaag gcatccgcgggccagatcagtgtgcaac-
ctacattctcagtgcaacggaatctcccttttt gaaagagcaaccgttatg-
gcagctttcagcgggaacaatgagggacgcacatcagacatg
cgaacggaagttataaggatgatggaaagcgcaaagccagaagatttgt-
ccttcca- gggg cggggagtcttcgagctctctgac-
gaaaaggcaacgaacccgatcgtgccttcctttgac atgagtaat-
gaagggtcttatttcttcggagacaatgcagaggagtatga (SEQ. ID No. 2).

Immunoassays

Plaque assays to evaluate recombinant protein expression were performed in a manner similar to virus titrations, described above. For plaque purification, however, a live immunostaining procedure was employed, i.e. virus-infected plates were not fixed. All other steps were the same.

Vaccination/Challenge

At 20–22 days of age, four groups of six caesarean-derived pigs, that were fed colostrum (COLOSTRIX™ Struve Labs) negative for SIV antibody, were vaccinated with $10^{8.0}$ PFU of the plaque-purified MVA/PR8 or MVA/SIV recombinant either intramuscularly (IM) or intranasally (IN). Immunization was repeated at 34–36 days of age. At 49–52 days of age, these twenty-four pigs and six unvaccinated controls were challenged oronasally with approximately 2 mls of homologous ISU field strain ($10^{6.9}$ $EID_{50}$/ml). A Saturn Nebulizer (Dynax), with an attached plastic face mask held over the animals' faces for 5 minutes, was used to deliver virus to the lower airways of the respiratory tract.

Virus Isolation and Titration

Nasal swabs were collected from all pigs at 2, 3, 4, and 5 days post-challenge and titrated in embryonated chicken eggs to determine levels of virus shedding. Nasal swab samples were vortex-mixed, then centrifuged at 400×g for 10 minutes, and the supernate used for egg inoculation. Ten-day-old embryonated eggs were inoculated in the allantoic cavity with 0.1 ml of sample and incubated at 37° for 72 hr. The harvested allantoic fluids were tested for HA activity. Eggs were inoculated in duplicate to determine the presence of virus. Samples found to be positive for virus were then titrated. For titration, four eggs were inoculated with each dilution and the results tabulated using the method of Spearman-Karber. (Finney D J. Spearman-Karber and moving averages. Statistical method in biological assay. 3rd ed. London: Charles Griffin & Company Ltd; 1978. p 394–401. Karber G. Beitrag zur kollektiven behandlung pharmakologischer reihenversuche. Arch Exp Pathol Pharmakol 1931;162:480–3. Schmidt N J, Emmons R W. General principles of laboratory diagnostic methods for viral, rickettsial, and chlamydial infections. Schmidt N J, Emmons R W, eds. Diagnostic procedures for viral, rickettsial, and chlamydial infections. 6th ed. Washington, D.C.: American Public Health Association; 1989. p 1–35.)

Serological Assays

Serum samples were harvested prior to first vaccination, second vaccination, challenge, and euthanasia, then analyzed by hemagglutination inhibition (HAI) against the two strains of influenza virus, strains PR8 and ISU, and by serum neutralization (SN) of MVA and SIV, using the constant virus-varying serum method.

HA and HAI tests were performed in 96-well microtiter plates, using 0.5% chicken erythrocytes. For the SIV and PR8 HAI assay, sera were pretreated using 10% kaolin and 5% washed chicken erythrocytes, then evaluated at 1:10 or greater dilutions against standardized live virus antigen. For these assays, four HA units of each virus were used to determine serum HAI titers.

The MVA SN procedure used 96-well plates containing 24-hour-old monolayers of CEF cells, inoculated with 50 ul of a 1:1 mixture of virus and 5-fold dilutions of serum, previously incubated at 37° C. for 1 hour. The inoculum was decanted after 1 hour, replaced with 200 ul of M199/F-10 media, supplemented as above but with only 0.5% FBS, and read at 5–7 days by CPE. SN titers were determined by the method of Reed-Muench. (Reed L J, Muench H. A simple method of estimating 50% endpoints. American Journal of Hygiene 1938;27:493-7. Schmidt N J, Emmons R W. General principles of laboratory diagnostic methods for viral, rickettsial, and chlamydial infections. Schmidt N J, Emmons R W, eds. Diagnostic procedures for viral, rickettsial, and chlamydial infections. 6th ed. Washington, D.C.: American Public Health Association; 1989. p 1–35.)

The SIV SN procedure is the same as that used for the MVA SN assay, except for the use of the ST cell line, a different maintenance medium (MEM and Earle's salts with no FBS), and centrifugation, as described above.

Post Mortem Examination

Following euthanasia, lungs were examined grossly and histologically for lesions. Tissues were fixed in 10% formalin, processed to paraffin blocks, and mounted on poly-L lysine coated glass slides. An immunohisto-chemical procedure, using a monoclonal antibody produced in mice against influenza viral nucleoprotein, was employed to determine the presence of viral antigen in lung tissue.

Results

Vaccination/Challenge

Different clinical signs were assigned a numerical value (table 1a) and scored (table 1b), with the nonvaccinates having far more signs than the vaccinates, including marked anorexia (not scored). The MVA/SIV vaccinates especially seemed unaffected by the challenge. Upon necropsy, they had very little to no gross or histopathological lung lesions, and little to no virus present in the lung as determined by immunohistochemistry (table 2).

TABLE 1a

Scoring of clinical signs during days 1–5 post-challenge

| Clinical signs noted | points/day |
|---|---|
| Nasal and Ocular discharge | |
| serous | 1 |
| slight mucopurulent | 2 |
| moderate mucopurulent | 3 |
| heavy mucopurulent | 4 |
| Depression, coughing, sneezing and abnormal breathing | |
| mild | 1 |
| moderate | 2 |
| severe | 3 |
| gauntness, dehydration | 1 |
| temperature >104.5 | 1 |

TABLE 1b

Results of scoring

| Group: | I | II | III | IV | V |
|---|---|---|---|---|---|
| nasal discharge | 2 | | | | |
| depression | 30 | | | 2 | |
| coughing | 3 | 2 | | 3 | |
| sneezing | 11 | 1 | 1 | 4 | |
| abnormal breathing | 16 | 3 | | | |
| fever >104.5 | 7 | 2 | | | |
| Total: | 69 | 8 | 1 | 9 | 0 |

Groups:

I=challenged nonvaccinated pigs, II=MVA/PR8 IM vaccinates, III=MVA/SIV IM vaccinates, IV=MVA/PR8 IN vaccinates and V=MVA/SIV IN vaccinates.

The gross lesions were most severe in non-vaccinated pigs, with total lung involvement of 2–30%, involving nearly the entire cranial and middle lung lobes. Lesions of similar extent and distribution were seen in PR8 IM and IN pigs with <10% total lung involvement in 5 of 6 pigs and 15% in 1 of 6 in each group. One pig in the PR8 IM group had almost no lesions; one pig in the PR8 IN group had lesions nearly as extensive as in some non-vaccinates. There were only minimal lesions in the tips of the middle lobes in 2 of 6 ISU IN pigs, with no lesions at all in the other 4 of 6 ISU IN pigs or in the ISU IM pigs.

TABLE 2

Summary of results from vaccination/challenge study. 1–5 days post-challenge

| Variable | I | II | III | IV | V |
|---|---|---|---|---|---|
| Virus isolations d 2–5, N = 6 | 23 | 20 | 11 | 15 | 7 |
| # shedding IN 4DPC | 6/6 | 6/6 | 1/6 | 6/6 | 3/6 |
| # shedding IN 5DPC | 5/6 | 2/6 | 1/6 | 0/6 | 0/6 |
| Ave IN titer/ml 4DPC ($log_{10}$) | 3 | 2 | $\leqq$0.8 | 1.5 | $\leqq$0.5 |
| # with gross lung lesions | 6/6 | 6/6 | 0/6 | 6/6 | 2/6 |
| % lung involved | 2–30% | <10% 1 with 15% | 0 | <10% 1 with 15% | minimal |

TABLE 2-continued

Summary of results from vaccination/challenge study. 1–5 days post-challenge

| Variable | I | II | III | IV | V |
|---|---|---|---|---|---|
| Virus in lung (IHC) | 6/6 | 3/6* | 0/6 | 0/6 | 2/6* |
| Histopath. lung lesions | 6/6 | 6/6 | 1/6 | 6/6 | 3/6 |

IN = intranasal, DPC = days postchallenge, IHC = immunohistochemistry, and * = small amount.

Microscopic lesions typical of those seen in SIV infection were found in the nonvaccinates, with active necrosis of bronchiolar epithelium and proliferative lesions of repair continuing 5 days after infection, particularly in the smaller bronchioles. There were lesions of similar character but much more focal in PR8 IN pigs. Lesions were also more characteristic of the repair stage, with minimal active necrosis in these pigs. There were similar mild lesions in 2 ISU IN pigs, though one had more severe lesions. There were no lesions in the other 3 ISU IN pigs or in the ISU IM pigs, with one small exception, a pig who had 2 small foci in a cranial lobe. In general, although gross lesions in PR8 IM and IN pigs appeared similar microscopically, damage in the IM-vaccinated pigs was less severe. Microscopic lesions were almost non-existent in ISU IM pigs but were focally present, though mild, in some ISU IN pigs.

Immunohistochemistry: The most extensive infecton of cells was detected in non-vaccinates. This correlates with the presence of active ongoing necrosis of epithelium in these pigs. Virus was also present in the alveoli in these pigs. There was a dramatic reduction in virus in all vaccinated pigs. Although there were more lesions induced in pigs vaccinated with PR8 than in pigs vaccinated with ISU by the corresponding route, virus is apparently cleared more rapidly in vaccinated pigs regardless of the MVA constructs employed.

Virus Isolations and Titrations

Nonvaccinates continued to shed virus through day 5 after challenge. In contrast, vaccinates, with the exception of the PR8 IM group, shed virus for a shorter period of time and at much lower titers (table 2).

Serological Assays

Serum HAI titers were higher in MVA/PR8 IM vaccinates than in the MVA/PR8 IN group, but this was not so evident in the MVA/ISU groups. Detectable titers did not appear in the MVA/ISU vaccinates until 14 days after the second vaccination. These were boosted by the SIV challenge as early as 5 days postchallenge, unlike those of the MVA/PR8 groups (table 3). The SN titers for both MVA and SIV were very low prechallenge. At 5 days postchallenge, all vaccinated groups had some SIV SN titer developing (table 4).

TABLE 3

Immune response in pigs as measured by GMT of HAI titers: pig sera vs. PR8 and ISU antigen

| | | Day 0 PV1 c. 21 do | | 14 DPV1 Day 0 PV2 | | −1 Day PC c. 14 DPV2 | | 5 Days PC c. 56 do | |
|---|---|---|---|---|---|---|---|---|---|
| Grp | #pigs | PR8 | ISU | PR8 | ISU | PR8 | ISU | PR8 | ISU |
| I | 6 | — | — | — | — | — | — | — | — |
| PR8-IM | 6 | — | — | 22 | — | 508 | — | 452 | — |
| ISU-IM | 6 | — | — | — | — | — | 57 | — | 113 |
| PR8-IN | 6 | — | — | 2 | — | 27 | — | 34 | — |

TABLE 3-continued

Immune response in pigs as measured by GMT of HAI titers: pig sera vs. PR8 and ISU antigen

| | | Day 0 PV1 c. 21 do | | 14 DPV1 Day 0 PV2 | | −1 Day PC c. 14 DPV2 | | 5 Days PC c. 56 do | |
|---|---|---|---|---|---|---|---|---|---|
| Grp | #pigs | PR8 | ISU | PR8 | ISU | PR8 | ISU | PR8 | ISU |
| ISU-IN | 6 | — | — | — | — | — | 40 | — | 160 |
| NEG C | 2 | — | — | — | — | nd | nd | — | — |

PV1 = postvaccination 1; PC = postchallenge; PV2 = postvaccination 2; do = days old; Grp 1 = Challenge Control

TABLE 4

Immune response in pigs as measured by GMT of serum neutralization titers. Pig sera vs. MVA and SIV antigen.

| | | Day 0 PV1 c. 21 do | | 14 DPV1 Day 0 PV2 | | −1 Day PC c. 14 DPV2 | | 5 Days PC C.56 do | |
|---|---|---|---|---|---|---|---|---|---|
| Grp | #pigs | MVA | SIV | MVA | SIV | MVA | SIV | MVA | SIV |
| I | 6 | — | — | — | — | — | — | — | — |
| PR8-IM | 6 | — | — | — | — | 1.41 | — | 1.3 | 4.5 |
| ISU-IM | 6 | — | — | — | — | — | 2.1 | 1.3 | 7.0 |
| PR8-IN | 6 | — | — | — | — | — | — | — | 5.2 |
| ISU-IN | 6 | — | — | — | — | — | 1.3 | — | 3.9 |
| NEG C | 2 | — | — | — | — | — | — | — | — |

PV1 = postvaccination 1; PC = postchallenge; PV2 = postvaccination 2, do = days old Grp I = challenge control Nucleotide Sequence The ISU HA gene had 98% homology to the IN88 HA at the nucleotide level, but only 81% to PR8 HA. This represented 99% homology at the amino acid level between ISU and IN88 HA, but only 83% to PR8 HA. Comparisons of NP revealed that OSI and IN88 shared 96% nucleotide and 99% amino acid similarity; PR8 NP, when compared to ISU, showed 87% nucleotide and 92% amino acid homology. The differences between the two genes of IN88 and ISU did not appear to be at locations previously associated with changes in virulence, such as the cleavage site between H1 and H2.

Recombinant vaccinia virus may be prepared in the usual carriers used in vaccine production, such as phosphate buffered saline. For use intranasally the agents may be given in droplet form. However, for veterinary purposes, the intramuscular injection is advantageous, since it is difficult to get the animals to cooperate when agents are administered intranasally.

Additionally, the recombinant virus of the invention may be given orally in any form which will protect the organisms from destruction in the stomach, such as in microspheres or in carbonated solutions.

The recombinant MVA/ISU vaccine developed and evaluated may be administered by any route which gives rise to immune response to provide effective means to protect pigs and humans against typical U.S. strains of H1N1 SIV. Even when the HA gene of the insert is heterotypic to an infecting strain, as was the case for the MVA/PR8 construct, immunity generated against the type A NP can help reduce clinical signs and clear virus more rapidly

What we claim is:

1. A purified DNA containing at least one sequence chosen from:

atgaaggcaatactattagtcttgc-tatatacattcacagccgcaaatgcagacacatta tgtataggttatcatg-caaataattcaactgacactgttgatacagtactagaaaagaat gtaacag-taacacactctgttaaccttctagaagacagacataacggaaaactatgtaaa ctaagggggg tagccccattg-catttgggtaaatgtaacattgctggatggctcctggga aacccagaatgt-gaattactattcacagcaagctcatggtcttacattgtggaaacatct aact-cagacaatgggacatgttacccaggagatttcatcaattatgaagagctaa gagag cagttgagctcagtgtcat-catttgaaaggtttgagattttccccaaggcaagttcatgg cccaaccat-gaaacgaacagaggtgtgacggcagcatgtccttatgctggagcaaacagc
ttctacagaaatttaatatggctgg-
taaaaaaaggaaattcatacccaaagctcagcaaa tcctatgttaa-
caataaggagaaggaagtcctcgtgctatggggcattcaccatccacct
accagtactgaccaacaaagtctctac-
cagaatgcagatgcctatgtttttgtggggtca tcaaagtacaacaagaaat-
tcaagccagaaatagcaacaagacccaaggtgagaggtcaa gcagg-
gagaatgaactattactggacactagttgagcctggagacacaataacatt
cgaa gcaactggaaatctagtggtaccaa-
gatatgccttcgcaatgaaaagaggttctggatct ggtattatcatttca-
gatacaccagtccacgattgtaatacgacctgtcaaacacccaaa ggtgc-
tataaacaccagcctcccatttcagaatatacatccagtcacaattggagaa
tgt ccaaaatatgtcaaaagtacaaaat-
tgagaatggctacaggattaaggaatatcccgtct attcaatctaggggc-
ctgtttggagccattgctggctttattgaggggggggtggacagga atgata-
gatggatggtacggttatcaccatcaaaatgagcagggatcaggatatgc
agcc gaccgaaagagcacacagaatgccat-
tgacgggatcactaacaaagtaaactctgttatt gaaaagataaacaca-
caattcacagcagtgggtaaagaattcaaccacctggaaaaaaga ata-
gagaatttaaataaaaaggttgatgatggttttctggatgtttggacttacaat
gcc gaattgttggttctattggaaaatgaaa-
gaactttggattaccatgactcaaatgtgaag aacctatatgagaaagtaa-
gaagccagctaaaaaacaatgccaaggaaattggaaatggc
tgctttgaattttaccacaaatgtgat-
gacaagtgcatggagagcgttaaaaatgggact tatgattac-
cccaaatactcagaagaatcaaaac-
taaacagagaggagatagatggagta
aagctggaatcaacaaggatttacca-
gattttggcgatatattcaactgtcgccagttca ttggtacttgttagtctc-
cctgggagcaatcagtttctggatgtgctccaatgggtcttt acagtgca-
gaatatgtatttaaaattaggatttcagagacatga (SEQ. ID No: 1)

and atggcgtctcaaggcaccaaacgat-
catatgaacaaatggagactggtggggaacgccag gatgccacagaaat-
cagagcatctgtcggaagaatgattggtggaatcggaagattctac atc-
caaatgtgcactgaactcaaacttagtgattatgagggacgactaattcaa
aatagc ataacaatagagagaatggtgctctct-
gcttttgatgagagaaggaataaatacctagaa gagcatcccagtgctgg-
gaaggatcctaagaaaactggaggacccatatatagaagagta gacg-
gaaagtggatgagagaactcatcctttatgacaaagaagaaataaggaga
gtttgg cgccaagcaaacaatggtgaagatgcaa-
cagccggtcttactcatatcatgatttggcac tccaatctgaacgatgccac-
ctatcagagaacaagagcgcttgttcgcactggaatggat cccagaatgt-
gctctctaatgcaaggttcaacacttcccagaaggtctggggccgcaggt
gctgcagtgaaaggagttggaacaatag-
caatggagttaatcagaatgatcaaacgtgga atcaatgaccgaaact-
tctggaggggtgaaaatgggcgaaggacaaggattgcatatgaa agaat-
gtgcaatattctcaaaggaaagtttcagacagctgcccagagggcaatgat
ggat caagtaagagaaagtcggaacccag-
gaaatgctgaaattgaagatctcattttcctggca cggtcagcacttat-
tctaaggggggtcagttgcacataagtcttgcctgcctgcttgtgtg
tatgggcttgcagtagcaagtgggcat-
gactttgaaagagaaggatattcactggtcggg atagaccccttcaaat-
tacttcaaaacagtcaagtgttcagcctgatcagaccaaatgaa aac-
ccagcccacaaaagtcaattggtgtggatggcatgccactctgctgcattt
gaggat ttaagagtatcaagcttcataagagg-
gaagaaagtggttccaagaggaaagctttccaca agaggggttcagat-
tgcttcaaatgagaatgttgaagctatggactctagtaccctagaa ctaa-
gaagcagatactgggccataaggaccagaagcggaggaaataccaatc
aacagaag gcatccgcgggccagatcagtgtgcaac-
ctacattctcagtgcaacggaatctccctttt gaaagagcaaccgttatg-
gcagctttcagcgggaacaatgagggacgcacatcagacatg cgaacg-
gaagttataaggatgatggaaagcgcaaagccagaagatttgtccttcca
gggg cggggagtcttcgagctctctgac-
gaaaaggcaacgaacccgatcgtgccttcctttgac atgagtaat-
gaagggtcttatttcttcggagacaatgcagaggagtatga (SEQ. ID No: 2).

2. A recombinant vaccinia virus containing as an insert the sequence atgaaggcaatactattagtcttgc-
tatatacattcacagccgcaaatgcagacacatta tgtataggttatcatg-
caaataattcaactgacactgttgatacagtactagaaaagaat gtaacag-
taacacactctgttaaccttctagaagacagacataacggaaaactatgtaaa
ctaaggggggtagccccattg-
catttgggtaaatgtaacattgctggatggctcctggga aacccagaatgt-
gaattactattcacagcaagctcatggtcttacattgtggaaacatct aact-
cagacaatgggacatgttacccaggagatttcatcaattatgaagagctaa
gagag cagttgagctcagtgtcat-
catttgaaaggtttgagattttccccaaggcaagttcatgg cccaaccat-
gaaacgaacagaggtgtgacggcagcat-
gtccttatgctggagcaaacagc
ttctacagaaatttaatatggctgg-
taaaaaaaggaaattcatacccaaagctcagcaaa tcctatgttaa-
caataaggagaaggaagtcctcgtgctatggggcattcaccatccacct
accagtactgaccaacaaagtctctac-
cagaatgcagatgcctatgtttttgtggggtca tcaaagtacaacaagaaat-
tcaagccagaaatagcaacaagacccaaggtgagaggtcaa gcagg-
gagaatgaactattactggacactagttgagcctggagacacaataacatt
cgaa gcaactggaaatctagtggtaccaa-
gatatgccttcgcaatgaaaagaggttctggatct ggtattatcatttca-
gatacaccagtccacgattgtaatacgacctgtcaaacacccaaa ggtgc-
tataaacaccagcctcccatttcagaatatacatccagtcacaattggagaa
tgt ccaaaatatgtcaaaagtacaaaat-
tgagaatggctacaggattaaggaatatcccgtct attcaatctaggggc-
ctgtttggagccattgctggctttattgaggggggggtggacagga atgata-
gatggatggtacggttatcaccatcaaaatgagcagggatcaggatatgc
agcc gaccgaaagagcacacagaatgccat-
tgacgggatcactaacaaagtaaactctgttatt gaaaagataaacaca-
caattcacagcagtgggtaaagaattcaaccacctggaaaaaaga ata-
gagaatttaaataaaaaggttgatgatggttttctggatgtttggacttacaat
gcc gaattgttggttctattggaaaatgaaa-
gaactttggattaccatgactcaaatgtgaag aacctatatgagaaagtaa-
gaagccagctaaaaaacaatgccaaggaaattggaaatggc
tgctttgaattttaccacaaatgtgat-
gacaagtgcatggagagcgttaaaaateggact tatgattac-
cccaaatactcagaagaatcaaaac-
taaacagagaggagatagatggagta
aagctggaatcaacaaggatttacca-
gattttggcgatatattcaactgtcgccagttca ttggtacttgttagtctc-
cctgggagcaatcagtttctggatgtgctccaatgggtcttt acagtgca-
gaatatgtatttaaaattaggatttcagagacatga (SEQ. ID No: 1).

3. A redombinant vaccinia virus containing the insert:

atggcgtctcaaggeaccaaacgat-
catatgaacaaatggagactggtggggaacgccag gatgccacagaaat-
cagagcatctgtcggaagaatgattggtggaatcggaagattctac atc-
caaatgtgcactgaactcaaacttagtgattatgagggacgactaattcaaa
atagc ataacaatagagagaatggtgctctct-
gcttttgatgagagaaggaataaatacctagaa gagcatcccagtgctgg-
gaaggatcctaagaaaactggaggacccatatatagaagagta gaeg-
gaaagtggatagaagaactcatcctttatgacaaagaagaaataaggaga
gtttgg cgccaagcaaacaatggtgaagatgcaa-
cagccggtcttactcatatcatgatttggcac tccaatctgaacgatgccac-
ctatcagagaacaagagcgcttgttcgcactggaatggat cccagaatgt-
gctctctaatgcaaggttcaacacttcccagaaggtctggggccgcaggt
gctgcagtgaaaggagttgguaaaatag-
caatggagttaatcagaatgatcaaacgtgga atcaatgaccgaaact-
tctggaggggtgaaaatgggcgaaggacaaggattgcatatgaa agaat-
gtgcaatattctcaaaggaaagtttcagacagctgcccagagggcaatgat
ggat caagtaagagaaagtcggaacccag-
gaaatgctgaaattgaagatctcattttcctggca cggtcagcacttat-
tctaaggggggtcagttgcacataagtcttgcctgcctgcttgtgtg
tatgggcttgcagtagcaagtgggcat-
gactttgaaagagaaggatattcactggtcggg atagaccccttcaaat-
tacttcaaaacagtcaagtgttcagcctgatcagaccaaatgaa aacccagcccacaaaagtcaattggtgtggatggcatgccactctgctgcattt
gaggat ttadgagtttcaagcttcataagagg-
gaagaaagtggttccaagaggaaagctttcacaa agaggggttcagat-
tgcttcaaatgagaatgttgaagctatggactctagtaccctagaa ctaa-
gaageagatactgggccataaggaccagaagcggaggaaataccaatc
aacagaag gcatccgcgggccagatcagtgtgcaac-
ctacattctcagtgcaacggaatctcccttt gaaagagcaaccgttatg-
gcagctttcagcgggaacaatgagggacgcacatcagacatg cgaacg-
gaagttataaggatgatggaaagcgcaaagccagaagatttgtccttcca
gggg cggggagtcttcgagctctctgac-
gaaaaggcaacgaacccgatcgtgccttcctttgac atgagtaat-
gaagggtcttatttcttcggagacaatgcagaggagtatga (SEQ. ID No: 2).

4. A recombinant vaccinia virus containing the inserts atgaaggcaatactattagtcttgc-
tatatacattcacagccgcaaatgcagacacatta tgtataggttatcatg-
caaataattcaactgacactgttgatacagtactagaaaagaat gtaacag-
taacacactctgttaaccttctagaagacagacataacggaaaactatgtaaa
ctaaggggggtagccccattg-
catttgggtaaatgtaacattgctggatggctcctggga aacccagaatgt-
gaattactattcacagcaagctcatggtcttacattgtggaaacatct aact-
cagacaatgggacatgttacccaggagatttcatcaattatgaagagctaa
gagag cagttgagctcagtgtcat-
catttgaaaggtttgagattttccccaaggcaagttcatgg cccaaccat-
gaaacgaacagaggtgtgacggcagcat-
gtccttatgctggagcaaacagc
ttctacagaaatttaatatggctgg-
taaaaaaaggaaattcatacccaaagctcagcaaa tcctatgttaa-
caataaggagaaggaagtcctcgtgctatggggcattcaccatccacct
accagtactgaccaacaaagtctctac-
cagaatgcagatgcctatgtttttgtggggtca tcaaagtacaacaagaaat-
tcaagccagaaatagcaacaagacccaaggtgagaggtcaa gcagg-
gagaatgaactattactggacactagttgagcctggagacacaataacatt
cgaa gcaactggaaatctagtggtaccaa-
gatatgccttcgcaatgaaaagaggttctggatct ggtattatcatttca-
gatacaccagtccacgattgtaatacgacctgtcaaacacccaaa ggtgc-
tataaacaccagcctcccatttcagaatatacatccagtcacaattggagaa
tgt ccaaaatatgtcaaaagtacaaaat-
tgagaatggctacaggattaaggaatatcccgtct attcaatctaggggc-
ctgtttggagccattgctggctttattgagggggggtggacagga atgata-
gatggatggtacggttatcaccatcaaaatgagcagggatcaggatatgc
agcc gaccgaaagagcacacagaatgccat-
tgacgggatcactaacaaagtaaactctgttatt gaaaagataaacaca-
caattcacagcagtgggtaaagaattcaaccacctggaaaaaaga ata-
gagaatttaaataaaaaggttgatgatggttttctggatgtttggacttacaat
gcc gaattgttggttctattggaaaatgaaa-
gaactttggattaccatgactcaaatgtgaag aacctatatgagaaagtaa-
gaagccagctaaaaaacaatgccaaggaaattggaaatggc
tgctttgaattttaccacaaatgtgat-
gacaagtgcatggagagcgttaaaaatgggact tatgattac-
cccaaatactcagaagaatcaaaac-
taaacagagaggagatagatggagta
aagctggaatcaacaaggatttacca-
gattttggcgatatattcaactgtcgccagttca ttggtacttgttagtctc-
cctgggagcaatcagtttctggatgtgctccaatgggtcttt acagtgca-
gaatatgtatttaaaattaggatttcagagacatga (SEQ. ID No: 1)

and atggcgtctcaaggcaccaaacgat-
catatgaacaaatggagactggtggggaacgccag gatgccacagaaat-
cagagcatctgtcggaagaatgattggtggaatcggaagattctac atc-
caaatgtgcactgaactcaaacttagtgattatgagggacgactaattcaa
aatagc ataacaatagagagaatggtgctctct-
gcttttgatgagagaaggaataaatacctagaa gagcatcccagtgctgg-
gaaggatcctaagaaaactggaggacccatatatagaagagta gacg-
gaaagtggatgagagaactcatcctttatgacaaagaagaaataaggaga
gtttgg cgccaagcaaacaatggtgaagatgcaa-
cagccggtcttactcatatcatgatttggcac tccaatctgaacgatgccac-
ctatcagagaacaagagcgcttgttcgcactggaatggat cccagaatgt-
gctctctaatgcaaggttcaacacttcccagaaggtctggggccgcaggt
gctgcagtgaaaggagttggaacaatag-
caatggagttaatcagaatgatcaaacgtgga atcaatgaccgaaact-
tctggaggggtgaaaatgggcgaaggacaaggattgcatatgaa agaat-
gtgcaatattctcaaaggaaagtttcagacagctgcccagagggcaatgat
ggat caagtaagagaaagtcggaacccag-
gaaatgctgaaattgaagatctcattttcctggca cggtcagcacttat-
tctaagggggtcagttgcacataagtcttgcctgcctgcttgtgtg
tatgggcttgcagtagcaagtgggcat-
gactttgaaagagaaggatattcactggtcggg atagaccccttcaaat-
tacttcaaaacagtcaagtgttcagcctgatcagaccaaatgaa aac-
ccagcccacaaaagtcaattggtgtggatggcatgccactctgctgcattt
gaggat ttaagagtatcaagcttcataagagg-
gaagaaagtggttccaagaggaaagctttccaca agaggggttcagat-
tgcttcaaatgagaatgttgaagctatggactctagtaccctagaa ctaa-
gaagcagatactgggccataaggaccagaagcggaggaaataccaatc
aacagaag gcatccgcgggccagatcagtgtgcaac-
ctacattctcagtgcaacggaatctcccttt gaaagagcaaccgttatg-
gcagctttcagcgggaacaatgagggacgcacatcagacatg cgaacg-
gaagttataaggatgatggaaagcgcaaagccagaagatttgtccttcca
gggg cggggagtcttcgagctctctgac-
gaaaaggcaacgaacccgatcgtg ccttcctttgaca—
tgagtaatgaagggtcttatttcttcggagacaatgcagaggagtatga
(SEQ. ID No: 2).

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
(A) LENGTH: 1724 base pairs
(B) TYPE: nucleic acid
(C) STRANDEDNESS: unknown
(D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO: 1:

```
ATGAAGGCAA TACTATTAGT CTTGCTATAT ACATTCACAG CCGCAAATGC AGACACATTA     60
TGTATAGGTT ATCATGCAAA TAATTCAACT GACACTGTTG ATACAGTACT AGAAAAGAAT    120
GTAACAGTAA CACACTCTGT TAACCTTCTA GAAGACAGAC ATAACGGAAA ACTATGTAAA    180
CTAAGGGGGG TAGCCCCATT GCATTTGGGT AAATGTAACA TTGCTGGATG GCTCCTGGGA    240
AACCCAGAAT GTGAATTACT ATTCACAGCA AGCTCATGGT CTTACATTGT GGAAACATCT    300
AACTCAGACA ATGGGACATG TTACCCAGGA GATTTCATCA ATTATGAAGA GCTAAGAGAG    360
CAGTTGAGCT CAGTGTCATC ATTTGAAAGG TTTGAGATTT TCCCCAAGGC AAGTTCATGG    420
CCCAACCATG AAACGAACAG AGGTGTGACG GCAGCATGTC CTTATGCTGG AGCAAACAGC    480
TTCTACAGAA ATTTAATATG GCTGGTAAAA AAAGGAAATT CATACCCAAA GCTCAGCAAA    540
TCCTATGTTA ACAATAAGGA GAAGGAAGTC CTCGTGCTAT GGGGCATTCA CCATCCACCT    600
ACCAGTACTG ACCAACAAAG TCTCTACCAG AATGCAGATG CCTATGTTTT TGTGGGGTCA    660
TCAAAGTACA ACAAGAAATT CAAGCCAGAA ATAGCAACAA GACCCAAGGT GAGAGGTCAA    720
GCAGGGAGAA TGAACTATTA CTGGACACTA GTTGAGCCTG GAGACACAAT AACATTCGAA    780
GCAACTGGAA ATCTAGTGGT ACCAAGATAT GCCTTCGCAA TGAAAAGAGG TTCTGGATCT    840
GGTATTATCA TTTCAGATAC ACCAGTCCAC GATTGTAATA CGACCTGTCA AACACCCAAA    900
GGTGCTATAA ACACCAGCCT CCCATTTCAG AATATACATC CAGTCACAAT TGGAGAATGT    960
CCAAAATATG TCAAAAGTAC AAAATTGAGA ATGGCTACAG GATTAAGGAA TATCCCGTCT   1020
ATTCAATCTA GGGGCCTGTT TGGAGCCATT GCTGGCTTTA TTGAGGGGGG GTGGACAGGA   1080
ATGATAGATG GATGGTACGG TTATCACCAT CAAAATGAGC AGGGATCAGG ATATGCAGCC   1140
GACCGAAAGA GCACACAGAA TGCCATTGAC GGGATCACTA ACAAAGTAAA CTCTGTTATT   1200
GAAAAGATAA ACACACAATT CACAGCAGTG GGTAAAGAAT TCAACCACCT GGAAAAAAGA   1260
ATAGAGAATT TAAATAAAAA GGTTGATGAT GGTTTTCTGG ATGTTTGGAC TTACAATGCC   1320
GAATTGTTGG TTCTATTGGA AAATGAAAGA ACTTTGGATT ACCATGACTC AAATGTGAAG   1380
AACCTATATG AGAAAGTAAG AAGCCAGCTA AAAAACAATG CCAAGGAAAT TGGAAATGGC   1440
TGCTTTGAAT TTTACCACAA ATGTGATGAC AAGTGCATGG AGAGCGTTAA AAATGGGACT   1500
TATGATTACC CCAAATACTC AGAAGAATCA AAACTAAACA GAGAGGAGAT AGATGGAGTA   1560
AAGCTGGAAT CAACAAGGAT TTACCAGATT TTGGCGATAT ATTCAACTGT CGCCAGTTCA   1620
TTGGTACTTG TTAGTCTCCC TGGGAGCAAT CAGTTTCTGG ATGTGCTCCA ATGGGTCTTT   1680
```

-continued

```
ACAGTGCAGA ATATGTATTT AAAATTAGGA TTTCAGAGAC ATGA                1724

(2) INFORMATION FOR SEQ ID NO: 2:

     (i) SEQUENCE CHARACTERISTICS:
          (A) LENGTH: 1490 base pairs
          (B) TYPE: nucleic acid
          (C) STRANDEDNESS: unknown
          (D) TOPOLOGY: unknown

    (ii) MOLECULE TYPE: DNA (genomic)

   (iii) HYPOTHETICAL: NO

    (iv) ANTI-SENSE: NO

    (xi) SEQUENCE DESCRIPTION: SEQ ID NO: 2:

ATGGCGTCTC AAGGCACCAA ACGATCATAT GAACAAATGG AGACTGGTGG GGAACGCCAG     60

GATGCCACAG AAATCAGAGC ATCTGTCGGA AGAATGATTG GTGGAATCGG AAGATTCTAC    120

ATCCAAATGT GCACTGAACT CAAACTTAGT GATTATGAGG GACGACTAAT TCAAAATAGC    180

ATAACAATAG AGAGAATGGT GCTCTCTGCT TTTGATGAGA GAAGGAATAA ATACCTAGAA    240

GAGCATCCCA GTGCTGGGAA GGATCCTAAG AAAACTGGAG GACCCATATA TAGAAGAGTA    300

GACGGAAAGT GGATGAGAGA ACTCATCCTT TATGACAAAG AAGAAATAAG GAGAGTTTGG    360

CGCCAAGCAA ACAATGGTGA AGATGCAACA GCCGGTCTTA CTCATATCAT GATTTGGCAC    420

TCCAATCTGA ACGATGCCAC CTATCAGAGA ACAAGAGCGC TTGTTCGCAC TGGAATGGAT    480

CCCAGAATGT GCTCTCTAAT GCAAGGTTCA ACACTTCCCA GAAGGTCTGG GGCCGCAGGT    540

GCTGCAGTGA AAGGAGTTGG AACAATAGCA ATGGAGTTAA TCAGAATGAT CAAACGTGGA    600

ATCAATGACC GAAACTTCTG GAGGGGTGAA AATGGGCGAA GGACAAGGAT TGCATATGAA    660

AGAATGTGCA ATATTCTCAA AGGAAAGTTT CAGACAGCTG CCCAGAGGGC AATGATGGAT    720

CAAGTAAGAG AAAGTCGGAA CCCAGGAAAT GCTGAAATTG AAGATCTCAT TTTCCTGGCA    780

CGGTCAGCAC TTATTCTAAG GGGGTCAGTT GCACATAAGT CTTGCCTGCC TGCTTGTGTG    840

TATGGGCTTG CAGTAGCAAG TGGGCATGAC TTTGAAAGAG AAGGATATTC ACTGGTCGGG    900

ATAGACCCCT TCAAATTACT TCAAAACAGT CAAGTGTTCA GCCTGATCAG ACCAAATGAA    960

AACCCAGCCC ACAAAAGTCA ATTGGTGTGG ATGGCATGCC ACTCTGCTGC ATTTGAGGAT   1020

TTAAGAGTAT CAAGCTTCAT AAGAGGGAAG AAAGTGGTTC CAAGAGGAAA GCTTTCCACA   1080

AGAGGGGTTC AGATTGCTTC AAATGAGAAT GTTGAAGCTA TGGACTCTAG TACCCTAGAA   1140

CTAAGAAGCA GATACTGGGC CATAAGGACC AGAAGCGGAG GAAATACCAA TCAACAGAAG   1200

GCATCCGCGG GCCAGATCAG TGTGCAACCT ACATTCTCAG TGCAACGGAA TCTCCCTTTT   1260

GAAAGAGCAA CCGTTATGGC AGCTTTCAGC GGGAACAATG AGGGACGCAC ATCAGACATG   1320

CGAACGGAAG TTATAAGGAT GATGGAAAGC GCAAAGCCAG AAGATTTGTC CTTCCAGGGG   1380

CGGGGAGTCT TCGAGCTCTC TGACGAAAAG GCAACGAACC CGATCGTGCC TTCCTTTGAC   1440

ATGAGTAATG AAGGGTCTTA TTTCTTCGGA GACAATGCAG AGGAGTATGA             1490
```